United States Patent
Born et al.

(10) Patent No.: US 10,501,450 B2
(45) Date of Patent: Dec. 10, 2019

(54) ANHYDRATE-FREE POLYMORPHICALLY PURE MICRONIZED CRYSTALLINE BREXPIPRAZOLE DI-HYDRATE FOR USE IN INTRAMUSCULAR INJECTABLE SUSTAINED RELEASE FORMULATIONS

(71) Applicant: HEXAL AG, Holzkirchen (DE)

(72) Inventors: Max Born, Holzkirchen (DE); Christoph Langes, Innsbruck (AT); Hannes Lengauer, Kundl (AT)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 16/073,366

(22) PCT Filed: Jan. 31, 2017

(86) PCT No.: PCT/EP2017/052005
§ 371 (c)(1),
(2) Date: Jul. 27, 2018

(87) PCT Pub. No.: WO2017/134038
PCT Pub. Date: Aug. 10, 2017

(65) Prior Publication Data
US 2019/0047994 A1 Feb. 14, 2019

(30) Foreign Application Priority Data
Feb. 1, 2016 (EP) .................... 16153668

(51) Int. Cl.
*C07D 409/12* (2006.01)
(52) U.S. Cl.
CPC ........ *C07D 409/12* (2013.01); *C07B 2200/13* (2013.01)

(58) Field of Classification Search
None
See application file for complete search history.

(56) References Cited

U.S. PATENT DOCUMENTS

2015/0086632 A1  3/2015  Sato et al.

FOREIGN PATENT DOCUMENTS

| WO | 2006112464 A1 | 10/2006 |
| WO | 2013162046 A1 | 10/2013 |
| WO | 2013162048 A1 | 10/2013 |

OTHER PUBLICATIONS

International Search Report and Written Opinion for PCT/EP2017/052005, dated Aug. 10, 2017, 28 pages.
Loh, Zhi Hui, et al., Overview of milling techniques for improving the solubility of poorly water-soluble drugs, Asian Pharmaceutical Sciences, vol. 10, 2015, pp. 255-274.

*Primary Examiner* — Kamal A Saeed
(74) *Attorney, Agent, or Firm* — Luedeka Neely Group, P.C.

(57) ABSTRACT

The present invention relates to a brexpiprazole dihydrate crystalline form having a particle size distribution of d50 of at most 10 μm and less than 5% w/w of brexpiprazole anhydrate. The present invention also relates to a process for preparing this brexpiprazole dihydrate crystalline form and to pharmaceutical compositions thereof. The present invention also relates to a process for determining the absence of brexpiprazole anhydrate in this brexpiprazole dihydrate crystalline form. This brexpiprazole dihydrate crystalline form is used for the preparation of pharmaceutical compositions having delayed release properties upon intramuscular injection.

3 Claims, 3 Drawing Sheets

ANHYDRATE-FREE POLYMORPHICALLY PURE MICRONIZED CRYSTALLINE BREXPIPRAZOLE DI-HYDRATE FOR USE IN INTRAMUSCULAR INJECTABLE SUSTAINED RELEASE FORMULATIONS

This application is a Section 371 national phase entry of PCT application PCT/EP2017/052005, filed Jan. 31, 2017. This application also claims the benefit of the earlier filing date of European patent application 16153668.5, filed Feb. 1, 2016.

FIELD OF THE INVENTION

The present invention relates to a process for the preparation of brexpiprazole dihydrate in the form of crystalline material having a particle size distribution characterized by a d50 of at most 10 µm, wherein a size reduction step is carried out in the presence of water at temperatures below 50° C. and yields micronized brexpiprazole dihydrate which is substantially free from brexpiprazole anhydrate.

The present invention also relates to brexpiprazole dihydrate in the form of crystalline material having a particle size distribution characterized by a d50 of at most 10 µm, the crystalline material being essentially free from brexpiprazole anhydrate.

The present invention also relates to pharmaceutical composition comprising polymorphically pure micronized brexpiprazole dihydrate.

The present invention also relates to a process for evaluating one or more properties of micronized brexpiprazole dihydrate, wherein the properties are indicative that a batch from which the sample of brexpiprazole dihydrate was taken is suitable for the preparation of a pharmaceutical composition having delayed release properties upon intramuscular injection.

BACKGROUND OF THE INVENTION

7-[4-[4-(1-Benzothiophen-4-yl)piperazin-1-yl]butoxy]quinolin-2(1H)-one (brexpiprazole; compound I) is an antidepressant and antipsychotic drug marketed under the brand Rexulti® for the oral treatment of schizophrenia and as an adjunctive treatment to antidepressants in major depressive disorder. REXULTI tablets are intended for oral administration and available in 0.25 mg, 0.5 mg, 1 mg, 2 mg, 3 mg and 4 mg strengths. The product was approved in the U.S. in 2015 for the aforementioned indications and is currently in phase III trials for the treatment of agitation associated with Alzheimer's disease and the treatment of PTSD (post-traumatic stress disorder).

(I)

Brexpiprazole is an atypical antipsychotic and shows partial agonist activity at serotonin 5-HT1A and dopamine D2 receptors, and antagonist activity at serotonin 5-HT2A receptors.

WO 2006/112464 A1 discloses brexpiprazole and its use for the treatment of schizophrenia and other central nervous system disorders. Brexpiprazole is described in example 1 as a crystalline material obtained as a white powder by recrystallization from ethanol.

WO 2013/162046 A1 characterizes the crystalline brexpiprazole obtained from example 1 of WO 2006/112464 A1 as an "anhydride", more properly to be understood as an "anhydrate" form of brexpiprazole. Brexpiprazole anhydrate, herein referred to as form I, shows characteristic PXRD reflections at 2 Theta angles of 14.4°, 19.1°, 20.2°, 21.3° and 23.2°. WO 2013/162046 A1 also discloses a crystalline hydrate of brexpiprazole which is characterized by means of PXRD. Brexpiprazole hydrate is described as showing characteristic PXRD reflections at 2 Theta angles of 7.7°, 9.4°, 11.8°, 18.9° and 24.0°. WO 2013/162046 A1 also discloses a crystalline dihydrate of brexpiprazole which is characterized by means of PXRD, Infrared spectroscopy, Raman-spectroscopy, and 1H-NMR. Brexpiprazole dihydrate is described as showing characteristic PXRD reflections at 2 Theta angles of 8.1°, 8.9°, 15.1°, 15.6° and 24.4°. An advantage of brexpiprazole dihydrate is described to be that when injected intramuscularly into rats, the dihydrate crystals can still be detected at the injection site, while the anhydrate form (form I) was no longer detectable 56 days after the injection. The brexpiprazole dihydrate crystals are thus suggested for injectable preparations of brexpiprazole with sustained release properties.

WO 2013/161830 A1 discloses an aqueous suspension comprising secondary particles formed by aggregation of brexpiprazole having a mean secondary particle diameter of 1 to 50 µm. A bulk powder is to be produced wherein brexpiprazole dihydrate should have a defined primary particle size. Milling and grinding are mentioned as methods for the preparation of the bulk powder.

Size reduction processes can expose the processed material to dry conditions and/or to elevated temperatures. A learning from WO 2013/162046 A1 is that the suitability of brexpiprazole for pharmaceutical preparations with sustained release properties is dependent on brexpiprazole being present as brexpiprazole dihydrate. The presence of a solid form which disappears more quickly than the dihydrate when applied intramuscularly could even compromise the desired delayed release effect, as a part of brexpiprazole would then dissolve more quickly upon intramuscular injection, leading to an undesired early peak in the brexpiprazole blood level.

SUMMARY OF THE INVENTION

The present inventors have discovered that brexpiprazole dihydrate can transform to brexpiprazole anhydrate form I at the conditions encountered during a size reduction process. In particular, processes where brexpiprazole dihydrate is processed at conditions with low water activity have been observed to be prone to cause dihydrate-anhydrate conversion. Thus, unless proper care is taken to maintain brexpiprazole dihydrate under conditions that assure its polymorphic stability, such as an aqueous environment, preferably at temperatures below 40° C., at least a part of brexpiprazole dihydrate can convert into brexpiprazole anhydrate form I and thus loses the necessary slow-release properties which are desirable for the preparation of a sustained release injectable pharmaceutical composition.

The present invention thus relates to a process for the preparation of brexpiprazole dihydrate in the form of crystalline material having a particle size distribution characterized by a d50 of at most 10 µm, wherein the process yields brexpiprazole dihydrate which is substantially free from brexpiprazole anhydrate. The process of the present invention maintains brexpiprazole dihydrate in the presence of water and preferably at temperatures of at most 40° C.

The present invention also relates to brexpiprazole dihydrate in the form of crystalline material having a particle size distribution characterized by a d50 of at most 10 µm, the crystalline material being essentially free from brexpiprazole anhydrate.

The present invention also relates to pharmaceutical composition comprising polymorphically pure micronized brexpiprazole dihydrate.

The present invention also relates to a process for evaluating one or more properties of micronized brexpiprazole dihydrate, wherein the properties are indicative that a batch from which the sample of brexpiprazole dihydrate was taken is suitable for the preparation of a pharmaceutical composition having delayed release properties upon intramuscular injection.

Definitions

In the context of the present invention the following abbreviations have the indicated meaning, unless explicitly stated otherwise:
PXRD powder X-ray diffraction/diffractogram
TGA thermogravimetric analyses
DSC differential scanning calorimetry
GMS gravimetric moisture sorption
RT room temperature
RH relative humidity
m mass
Δm mass change The main characteristics of a PXRD are 2θ position, peak height, peak area and shape (characterized by, for example, peak width or asymmetry, analytical function, empirical representation). In addition to the diffraction peaks, an X-ray diffraction experiment also generates a more-or-less uniform background, upon which the peaks are superimposed. Besides specimen preparation, other factors contribute to the background, for instance the sample holder, diffuse scattering from air and equipment, other instrumental parameters such as detector noise, general radiation from the X-ray tube, etc. The peak-to-background ratio can be increased by minimizing background and by choosing prolonged exposure times. In the context of the present invention, the term "peak" or "reflection" denotes a particular 2-Theta position, wherein the signal-to-noise ratio (calculated according to item 2.2.46 of the European Pharmacopoeia) is at least 3 to 1.

As used herein the term "room temperature" is understood to mean temperatures between 10 and 30° C., typically between 15° C. and 25° C. [see e.g. European Pharmacopoeia 8.3, 1.2 (2015)].

The term "non-hygroscopic" as used herein refers to compounds showing a mass change of less than 2% (w/w) based on the weight of the compound in the range of from 0 to 95% relative humidity at (25.0±0.1) ° C.

As used herein, the term "water activity" (aw) refers to the ratio of the vapor pressure of water in a liquid (p) to the vapor pressure of pure water (po) at the same temperature. Water activity can be expressed by the equation aw=p/po and hence ranges from 0.0 aw (no water is present) to 1.0 aw (pure water).

The term "essentially the same" with reference to PXRD means that variabilities in peak positions and relative intensities of the peaks are to be taken into account. For example, a typical precision of the 2-Theta values is in the range of ±0.2° 2-Theta. Thus, for example a diffraction peak that usually appears at 14.9° 2-Theta for example can appear between 14.7° and 15.1° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

The term "brexpiprazole dihydrate" as used herein refers to the crystalline form of brexpiprazole disclosed as "dihydrate" in WO 2013/162046 A1 which is characterized by having a PXRD comprising reflections at 2-Theta angles of 8.1°, 8.9°, 15.1°, 15.6° and 24.4°, and preferably further peaks at 2-Theta angles of 11.6°, 12.2°, 14.0°, 16.3°, 18.1°, 18.4°, 18.9° and 19.5°, when measured by copper Kalpha$_{1,2}$ radiation through a monochromator at a wavelength of 0.15418 nm. Brexpiprazole dihydrate can have a water content according to Karl Fischer of from 6.5 to 8.8 wt. %.

The brexpiprazole dihydrate can be micronized. The term "micronized" as used herein denotes that a certain matter (in the present invention brexpiprazole dihydrate) has been subjected to a size reduction process. The review-article "Overview of milling techniques for improving the solubility of poorly water-soluble drugs" (Asian Journal of Pharmaceutical Sciences, Vol. 10, Issue 4, July 2015, pages 255-274) gives an overview on milling techniques and also describes that apart from the particle size, micronization (in particular milling) also alters the surface roughness and shape of particles. For instance, milled particles are rarely spherical or isometric in shape. Milled particles can possess platelet-like shape or needle-shape. The shape of the particles can be determined by any suitable means that is known to a skilled person, e.g. by image analysis techniques, laser diffraction, scanning electron microscopy, transmission electron microscopy and atomic force microscopy. Thus, by analyzing the shape of the size-reduced particles, conclusions can be drawn whether said particle was subjected to a micronization step (size reduction step).

A micronization- or size-reduction process is a process that is carried out under controlled conditions. Within the meaning of the present invention, the micronization-process is controlled for instance with regard to the environment in which the micronization is carried out. As disclosed elsewhere herein, due care has to be taken that brexpiprazole dihydrate is kept in an environment with a sufficiently high water activity of at least 0.2, and preferably that brexpiprazole dihydrate is kept in an aqueous environment. Further preferred, temperatures above 45° C. are avoided.

The term "brexpiprazole anhydrate" as used herein refers to the crystalline form I of brexpiprazole anhydrate, disclosed as "anhydride" in WO 2013/162046 A1, which is characterized by having a PXRD comprising reflections at 2-Theta angles of 6.8°, 10.0°, 10.8°, 14.5°, 14.9°, 17.4°, 19.2°, 20.3°, 21.3° and 23.2° when measured by copper Kalpha$_{1,2}$ radiation through a monochromator at a wavelength of 0.15418 nm. The crystalline form I of brexpiprazole anhydrate can be prepared according to comparative example 1 of WO 2013/162046 A1

The term "brexpiprazole hydrate" as used herein refers to the crystalline form of brexpiprazole disclosed as "hydrate" in WO 2013/162046 A1 which is characterized by having a PXRD comprising reflections at 2-Theta angles of 7.7°, 9.4°, 11.8°, 18.9° and 24.0°, and preferably further peaks at 2-Theta angles of 5.7°, 8.1°, 8.8°, 10.7°, 12.6°, 13.6°, 13.9°, 15.0°, and 15.6°, when measured by copper Kapha$_{1,2}$ radiation through a monochromator at a wavelength of 0.15418 nm.

For the purpose of this invention, particle size distribution is determined as the percent volume at each particle size and measured by a laser diffraction method in the context of a circulating aqueous suspension. A Malvern Mastersizer 3000 laser diffraction analyzer equipped with a Hydro EV measurement cell was used. About 50 mg of sample were filled into a 15 ml glass test tube. The sample was wetted with two drops of Tween 80 and vortexed. Then the thoroughly wetted sample was dispersed in about 7 mL of UHQ-water by vortexing until the particles were dispersed. The suspension was treated for 7 minutes in an ultrasonification bath at RT (Elma S50H). The well dispersed suspension was then measured in water by adding a sample from the center of the test tube containing the well dispersed suspension to a water-filled dispersion unit prefilled with 70 mL of water. The sample in the 70 mL dispersion unit was kept under stirring at 2000 rpm. More sample from the test tube was added, until a targeted obscuration range of 10-25 percent was achieved. The Malvern Mastersizer was operated using the following parameters:

Background time—8 s.
Measurement time—12 s.
Refractive index dispersant—1.33
Stirring unit—2000 U/min (as mentioned above).
External sonification—5 min (as mentioned above)
Internal sonification—no.
Waiting period—3 Minutes.
Diffraction method—Fraunhofer theory.
Analysis model—general purpose.
Sensitivity—normal
Blue laser is on, results are by volume distribution.

Measurement occurred after an optical alignment of the laser was done and after a background measurement was run. A measurement sequence consisted of eight individual measurements for which the mean value was represented as a histogram.

d90 as used herein means that 90% of the particles (based on volume) are smaller than or equal to the indicated size.

d50 as used herein means that 50% of the particles (based on volume) are smaller than or equal to the indicated size.

d10 as used herein means that 10% of the particles (based on volume) are smaller than or equal to the indicated size.

As used herein, batch (or lot) refers to a specific quantity of material produced by a process or a series of processes to a final homogeneous state with specified limits and identified by a batch number and a material number. In the case of continuous production a batch may correspond to a defined fraction of the production. The batch size may be defined either by a fixed quantity or the amount produced in a fixed time interval.

A batch Number (or lot number) as used herein refers to a unique combination of numbers, letters, and/or symbols that identifies a batch (or lot) and from which the production and distribution history can be determined.

As used herein, the term "substantially pure" with reference to a particular polymorphic form means that a composition containing said polymorphic form includes less than 10%, more preferably less than 5%, such as less than 3%, most preferably less than 1% by weight of any other physical forms of the compound, w/w percentages being based upon the weight of the first polymorph.

Figure 4:
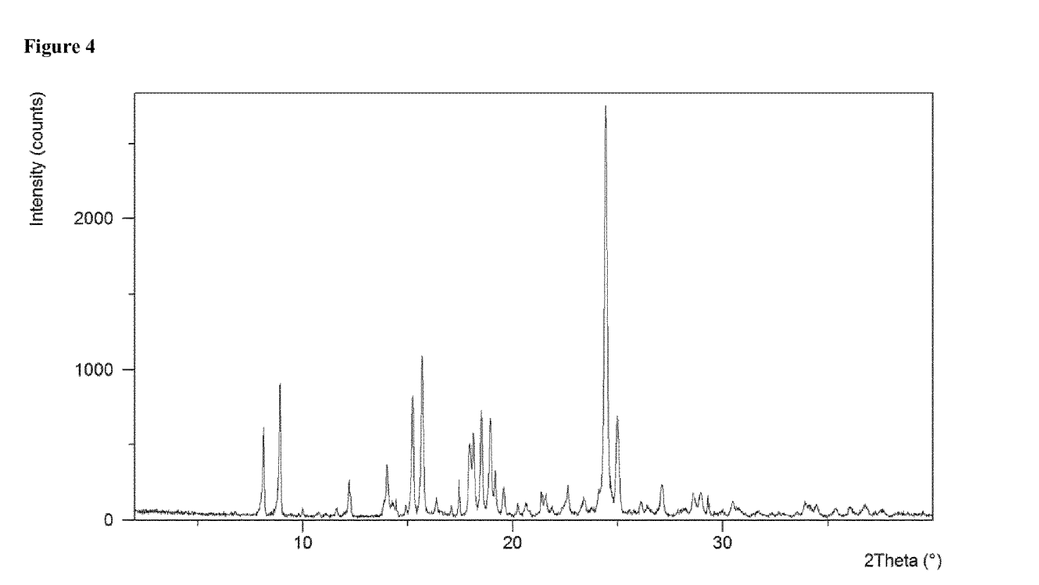
FIG. 4: Representative PXRD micronized brexpiprazole dihydrate of the present invention to which 10% brexpiprazole form I have been added In all figures the X-axis shows the 2-theta angle/°, with tick marks at indicated 2-theta angles. The Y-axis shows the intensity/counts, with tick marks, from bottom to top, at 1000, 2000. All PXRDs were recorded at 25° C. and 30% relative humidity.

"Absence of a peak" as used herein is defined as a peak having an intensity of at most 1%, such as 0.5% or 0.2%, of the highest peak in a PXRD of a sample of crystalline brexpiprazole dihydrate, more preferably no detectable PXRD peak above background signals. An example of a characteristic powder X-ray diffraction pattern of brexpiprazole dihydrate to which 10% of brexpiprazole anhydrate have been added is shown in FIG. 4.

DETAILED DESCRIPTION OF THE INVENTION

The invention is described below in further detail by embodiments, without being limited thereto.

In one aspect, the present invention relates to a micronized crystalline form of brexpiprazole, hereinafter also designated micronized "brexpiprazole dihydrate".

Brexpiprazole dihydrate has been described in WO2013/162046 A1 and can be prepared according to example 1 of WO2013/162046 A1.

Brexpiprazole dihydrate can for example be distinguished from two other forms described in WO 2013/162046 A1 by the position of reflections in its PXRD. Table 1 provides an overview of reflections for the dihydrate, the hydrate and the anhydrate form, respectively.

Unique reflections may be used to distinguish one crystalline form from the other.

TABLE 1

Different solid forms of brexpiprazole and their reflections

| Dihydrate Reflections [±0.2 °2Th.] | Hydrate Reflections [±0.2 °2Th.] | Anhydrate Reflections [±0.2 °2Th.] |
|---|---|---|
| 8.1 | 5.7 | 6.8 |
| 8.9 | 7.7 | 10.0 |
| 11.6 | 8.1 | 10.8 |
| 12.2 | 8.8 | 14.5 |
| 14.0 | 9.4 | 14.9 |
| 15.1 | 10.7 | 17.4 |
| 15.6 | 11.8 | 19.2 |
| 16.3 | 13.9 | 20.3 |
| 18.1 | 15.0 | 21.3 |
| 18.4 | 17.7 | 23.2 |
| 18.9 | 18.9 | |
| 19.5 | 19.8 | |
| 20.5 | 20.4 | |
| 23.3 | 22.2 | |
| 24.4 | 23.1 | |
| 25.0 | 25.2 | |

The present inventors have discovered that brexpiprazole dihydrate can transform to brexpiprazole anhydrate when processed under non-aqueous conditions and/or at elevated temperatures, for example during jet milling. Brexpiprazole anhydrate is more soluble than brexpiprazole dihydrate and also dissolves more quickly when injected into a mammalian body. Thus, a sample of brexpiprazole dihydrate can be compromised for use as an active pharmaceutical ingredient for a delayed release pharmaceutical composition, unless proper care is taken during storage and/or processing.

Thus, the present invention relates to brexpiprazole dihydrate in the form of crystalline material having a particle size distribution characterized by a d50 of at most 10 µm, the crystalline material comprising less than 5% w/w of brexpiprazole anhydrate in relation to the total amount of brexpiprazole, preferably the crystalline material comprising less than 3% w/w of brexpiprazole anhydrate, and most preferably comprising no detectable amount of brexpiprazole anhydrate.

The relative amount of brexpiprazole anhydrate in relation to the total amount of brexpiprazole can be determined by mixing defined amounts of pure crystalline brexpiprazole anhydrate, for example obtainable according to comparative example 1 of WO 2013/162046 A1, with defined amounts of pure crystalline brexpiprazole dihydrate, for example obtainable according to example production example 1 of CA 2871398 A1. In such a manner reference mixtures comprised of 5% w/w brexpiprazole anhydrate and 95% w/w brexpiprazole dihydrate or 3% w/w brexpiprazole anhydrate and 97% w/w brexpiprazole dihydrate or 1% w/w brexpiprazole anhydrate and 99% w/w brexpiprazole dihydrate can be prepared. The content w/w of brexpiprazole anhydrate can then be determined by taking a PXRD of the test sample and comparing it with the PXRDs of the reference mixtures.

The presence of brexpiprazole anhydrate can be detected by the presence of a PXRD peak at 6.8°+/−0.2° 2-Theta and/or the presence of a PXRD peak at 10.0+/−0.2° 2-Theta and/or the presence of a PXRD peak at 17.4+/−0.2° 2-Theta. Thus, optionally the brexpiprazole dihydrate in the form of crystalline material having a particle size distribution characterized by a d50 of at most 10 µm, preferably at most 9 µm, more preferably at most 8 µm, of the present invention can be characterized by the absence of a PXRD peak at 6.8°+/−0.2° 2-Theta and/or absence of a PXRD peak at 17.4°+/−0.2° 2-Theta.

Thus in a preferred aspect, the present invention relates to crystalline brexpiprazole dihydrate in form of crystalline material having a particle size distribution characterized by a d50 of at most 10 µm, such as at most 9 µm, for example at most 8 µm, having a PXRD comprising peaks at 2-theta angles of 8.1°, 8.9°, 15.1°, 15.6° and 24.4°, further characterized by the absence of peaks at 2-theta angles of 6.8°+/−0.2° and 17.4°+/−0.2°, when measured at room temperature with Copper Kalpha$_{1,2}$ radiation having a wavelength of 0.15418 nm.

Thus in another preferred aspect, the present invention relates to crystalline brexpiprazole dihydrate in form of crystalline material having a particle size distribution characterized by a d50 of at most 10 µm, such as at most 9 µm, for example at most 8 µm, having a PXRD comprising peaks at 2-theta angles of 8.1°, 8.9°, 15.1°, 15.6° and 24.4°, further characterized by the absence of peaks at 2-theta angles of 10.0°+/−0.2° and 17.4°+/−0.2°, when measured at room temperature with Copper Kalpha$_{1,2}$ radiation having a wavelength of 0.15418 nm.

Alternatively, the particle size distribution can be characterized by a d90 of from 10 µm to 25 µm, such as from 12 µm to 25 µm, or from 15 µm to 22 µm.

Alternatively, the particle size distribution can be characterized by a d50 of from 3 µm to 10 µm, such as from 4 µm to 9 µm, or from 4 µm to 8 µm.

Alternatively, the particle size distribution can be characterized by a d10 of from 400 nm to 3 µm, such as from 600 nm to 2.5 µm, or from 800 nm to 2.0 µm.

Alternatively, the particle size distribution can be characterized by a d90 of from 10 µm to 50 µm, by a d50 of from 3 µm to 10 µm, and by a d10 of from 400 nm to 3 µm.

Alternatively, the particle size distribution can be characterized by a d90 of from 12 µm to 30 µm, a d50 of from 3 µm to 10 µm, and a d10 of from 400 nm to 2.5 µm.

Alternatively, the particle size distribution can be characterized by a d90 of from 12 µm to 25 µm, a d50 of from 4 µm to 9 µm, and a d10 of from 800 nm to 2.0 µm.

The brexpiprazole dihydrate of the invention in the form of crystalline material having the described particle size distribution can be prepared by the process for the preparation of micronized brexpiprazole dihydrate of the invention.

In a further aspect the present invention relates to a process for the preparation of brexpiprazole dihydrate in the form of crystalline material having a particle size distribution characterized by a d50 of at most 10 µm comprising:
(i) providing brexpiprazole dihydrate in the form of crystalline material having a particle size distribution characterized by a d50 of at least 10 µm;
(ii) adding brexpiprazole dihydrate to an aqueous medium to form a suspension;
(iii) subjecting the aqueous suspension of brexpiprazole dihydrate to a size reduction means to obtain brexpiprazole dihydrate in the form of crystalline material having a particle size distribution characterized by a d50 of at most 10 µm.

Brexpiprazole dihydrate, for example as obtainable from production example 1 of CA 2871398 A1, is a preferred starting material for step (i). It is preferred that the particle size of the brexpiprazole dihydrate is already small enough to allow typical size reduction processes. For example brexpiprazole dihydrate can be sieved so as to remove very coarse material.

The brexpiprazole dihydrate can then be added to an aqueous medium in which it is hardly soluble to form a suspension. Brexpiprazole dihydrate is hardly soluble in water and has a solubility at 25° C. in water of 10 µg/mL, whereas brexpiprazole anhydrate under the same conditions has a solubility of 18 µg/mL.

Preferably the aqueous medium for forming the suspension in step (ii) is an alcohol/water mixture. Preferably the alcohol is a C1 to C4 alcohol.

The alcohol content of the medium of step (ii) is preferably at most 85% (v/v), preferably at most 80% v/v, such as at most 70%. Preferably, the solvent in (ii) comprises no additional organic solvent, most preferably the solvent in (ii) is essentially free of any additional organic solvent.

The medium in (ii) comprises water in an amount of at least 10% (v/v). Most preferably the aqueous medium consists of a mixture of a C1 to C4 alcohol, such as ethanol, and water, or pure water. A preferred ethanol/water mixture is at most 60% ethanol/at least 40% water, such as at most 40% ethanol/at least 60% water, for example such as at most 20% ethanol/at least 80% water. The medium in step (ii) can also be 100% water.

Preferably the concentration of the brexpiprazole dihydrate applied in (ii) is in the range of from 1% to 60% (w/w), more preferably from 2% to 30% and most preferably it is about 10%.

Subjecting the aqueous suspension of brexpiprazole dihydrate to a size reduction means can take the form of wet milling. Wet milling can be carried out by a dispersion mill, such as a ball mill, an attritor mill, a vibratory mill, a planetary mill and media mills, such as a bead mill.

The skilled person will appreciate that many different processes for the reduction of particle size may be used, provided that due care is taken to keep brexpiprazole dihydrate in an environment with a sufficiently high water activity of at least 0.2, preferably of at least 0.5, and preferably keeping brexpiprazole dihydrate in an aqueous environment, and preferably also avoiding temperatures above 45° C. Preferably (iii) takes the form of milling brexpiprazole dihydrate in the presence of an aqueous medium.

The preferred milling process of step (iii) is wet ball milling of a suspension of brexpiprazole dihydrate in an aqueous solvent mixture. Water has to be present during the milling process.

The temperature for the milling of step (iii) is preferably from −5° C. to 30° C., such as from −5° C. to 20° C. High temperatures should be avoided for brexpiprazole dihydrate and it advisable to process brexpiprazole dihydrate in the presence of water in the cold.

The obtained brexpiprazole dihydrate in the form of crystalline material having a particle size distribution characterized by a d50 of at most 10 μm can be collected by any conventional method such as filtration or centrifugation, most preferably by filtration.

Optionally, the isolated crystals obtained from (iii) may be washed with water.

In a further aspect, the present invention relates to at least two, more preferably three, such as four or even five, subsequent batches of brexpiprazole dihydrate in the form of crystalline material having a particle size distribution characterized by a d50 of at most 10 μm, such as at most 9 μm and for example at most 8 μm,
wherein the crystalline material comprising less than 5% w/w of brexpiprazole anhydrate in relation to the total amount of brexpiprazole, preferably the crystalline material comprising less than 3% of brexpiprazole anhydrate, and most preferably comprising no detectable amount of brexpiprazole anhydrate. Preferably all of the at least two, more preferably all of the three, such as all of the four or even all of the five subsequent batches comprise no detectable amount of brexpiprazole anhydrate.

In a further aspect, the present invention relates to at least two, more preferably three, such as four or even five, subsequent batches of brexpiprazole dihydrate in the form of crystalline material having a particle size distribution characterized by a d90 of at most 25 μm, for example at most 22 μm,
wherein the crystalline material comprising less than 5% w/w of brexpiprazole anhydrate in relation to the total amount of brexpiprazole, preferably the crystalline material comprising less than 3% of brexpiprazole anhydrate, and most preferably comprising no detectable amount of brexpiprazole anhydrate. Preferably all of the at least two, more preferably all of the three, such as all of the four or even all of the five subsequent batches comprise no detectable amount of brexpiprazole anhydrate.

In a further aspect, the present invention relates to at least two, more preferably three, such as four or even five, subsequent batches of brexpiprazole dihydrate in the form of crystalline material having a particle size distribution characterized by a d10 of at most 3 μm, such as at most 2.5 μm, for example at most 2.0 μm,
wherein the crystalline material comprising less than 5% w/w of brexpiprazole anhydrate in relation to the total amount of brexpiprazole, preferably the crystalline material comprising less than 3% of brexpiprazole anhydrate, and most preferably comprising no detectable amount of brexpiprazole anhydrate. Preferably all of the at least two, more preferably all of the three, such as all of the four or even all of the five subsequent batches comprise no detectable amount of brexpiprazole anhydrate.

Subsequent batches can be identified via batch numbers and information on the batch production history. An example for five subsequent batches of "D=brexpiprazole dihydrate" is the uninterrupted sequence D, D, D, D, D, where no batch of brexpiprazole with a different end product "A=brexpiprazole anhydrate" or "D/A=Mixture of brexpiprazole dihydrate and brexpiprazole anhydrate" intervenes the sequence.

In another aspect, the invention relates to the use of brexpiprazole dihydrate in the form of crystalline material having a particle size distribution characterized by a d90 of from 10 μm to 25 μm, such as from 12 μm to 25 μm, or from 15 μm to 22 μm,
or alternatively having a particle size distribution characterized by a d50 of from 3 μm to 10 μm, such as from 4 μm to 9 μm, or from 4 μm to 8 μm,
or alternatively having a particle size distribution characterized by a d10 of from 400 nm to 3 μm, such as from 600 nm to 2.5 μm, or from 800 nm to 2.0 μm,
or alternatively having a particle size distribution characterized by a d90 of from 12 μm to 25 μm, by a d50 of from 4 μm to 9 μm, and by a d10 of from 600 nm to 2.5 μm,
or alternatively having a particle size distribution characterized by a d90 of from 15 μm to 22 μm, a d50 of from 4 μm to 8 μm, and a d10 of from 800 nm to 2.0 μm, for the preparation of a pharmaceutical composition.

Preferably, brexpiprazole dihydrate in the form of crystalline material having a particle size distribution characterized by a d90 of from 10 μm to 25 μm, such as from 12 μm to 25 μm, or from 15 μm to 22 μm, or alternatively having a particle size distribution characterized by a d50 of from 3 μm to 10 μm, such as from 4 μm to 9 μm, or from 4 μm to 8 μm, or alternatively having a particle size distribution characterized by a d10 of from 400 nm to 3 μm, such as from 600 nm to 2.5 μm, or from 800 nm to 2.0 μm, or alternatively having a particle size distribution characterized by a d90 of from 10 μm to 25 μm, by a d50 of from 3 μm to 10 μm, and by a d10 of from 400 nm to 3 μm, or alternatively having a particle size distribution characterized by a d90 of from 12 μm to 25 μm, a d50 of from 4 μm to 9 μm, and a d10 of from 600 nm to 2.5 μm, or alternatively having a particle size distribution characterized by a d90 of from 15 μm to 22 μm, a d50 of from 4 μm to 8 μm, and a d10 of from 800 nm to 2.0 μm,
is used in the preparation of an injectable preparation, such as an aqueous suspension comprising brexpiprazole dihydrate.

The present invention therefore also relates to a pharmaceutical composition comprising brexpiprazole dihydrate in the form of crystalline material having a particle size distribution characterized by a d50 of at most 10 μm, for example a prefilled syringe that is prefilled with an aqueous suspension comprising brexpiprazole dihydrate in the form of crystalline material having a particle size distribution characterized by a d50 of at most 10 μm, such as brexpiprazole dihydrate in the form of crystalline material having a particle size distribution characterized by a d50 of from 3 μm to 10 μm, such as from 4 μm to 9 μm, or from 4 μm to 8 μm.

Alternatively the present invention therefore also relates to a pharmaceutical composition comprising brexpiprazole dihydrate in the form of crystalline material having a particle size distribution characterized by a d90 of at most 25 µm, for example a prefilled syringe that is prefilled with an aqueous suspension comprising brexpiprazole dihydrate in the form of crystalline material having a particle size distribution characterized by a d90 of at most 25 µm, such as brexpiprazole dihydrate in the form of crystalline material having a particle size distribution characterized by a d90 of from 10 µm to 25 µm, such as from 12 µm to 25 µm, or from 15 µm to 22 µm.

Alternatively the present invention therefore also relates to a pharmaceutical composition comprising brexpiprazole dihydrate in the form of crystalline material having a particle size distribution characterized by a d10 of at most 3 µm, for example a prefilled syringe that is prefilled with an aqueous suspension comprising brexpiprazole dihydrate in the form of crystalline material having a particle size distribution characterized by a d10 of at most 3 µm, such as brexpiprazole dihydrate in the form of crystalline material having a particle size distribution characterized by a d10 of from 400 nm to 3 µm, such as from 600 nm to 2.5 µm, or from 800 nm to 2.0 µm.

In a further aspect, the invention relates to a pharmaceutical composition comprising brexpiprazole dihydrate in the form of crystalline material having a particle size distribution characterized by a d50 of at most 10 µm—or comprising brexpiprazole dihydrate in the form of crystalline material having a particle size distribution as defined by any other value, range or combination of ranges above—and at least one pharmaceutically acceptable excipient.

The pharmaceutical composition comprising brexpiprazole dihydrate in the form of crystalline material having a particle size distribution characterized by a d50 of at most 10 µm of the invention—or comprising brexpiprazole dihydrate in the form of crystalline material having a particle size distribution as defined by any other value, range or combination of ranges above—is preferably a sterile injectable formulation. A sterile injectable formulation of the present invention can be produced, for example, as described in test example 4, examples C, D, E and F of CA 2871398 A1. A sterile injectable formulation of the present invention can also be produced, for example, as described in test example 5, examples G-1, G-2, G-3, G-4, G-5 and G-6 of CA 2871398 A1. A sterile injectable formulation of the present invention can also be produced, for example, as described in test example 5, examples H-1, H-2, H-3, H-4, H-5 and H-6 of CA 2871398 A1. A sterile injectable formulation of the present invention can also be produced, for example, as described in test example 5, examples I-1, I-2, I-3, I-4, I-5 and I-6 of CA 2871398 A1. A sterile injectable formulation of the present invention can also be produced, for example, as described in test example 5, examples J-1, J-2, J-3, J-4, J-5 and J-6 of CA 2871398 A1. The skilled person will appreciate that any reference to brexpiprazole dihydrate in CA 2871398 A1 is to be replaced by brexpiprazole dihydrate in the form of crystalline material having a particle size distribution characterized by a d50 of at most 10 µm of the present invention—or by brexpiprazole dihydrate in the form of crystalline material having a particle size distribution as defined by any other value, range or combination of ranges above.

For the preparation of sterile injectable formulations of the present invention, further reference is made to the passage from page 5, line 8 to page 11, line 28 of CA 2871398 A1, to page 22, line 14 to page 30, line 3 of CA 2871398 A1, to the passage from page 30, line 21 to page 34, line 24 of CA 2871398 A1, and to the passage from page 45, line 15 to page 50, line 5, with the proviso that any reference to "compound (I)", "anhydride" or "brexpiprazole dihydrate" in CA 2871398 A1 is to be replaced by brexpiprazole dihydrate in the form of crystalline material having a particle size distribution characterized by a d50 of at most 10 µm of the present invention—or by brexpiprazole dihydrate in the form of crystalline material having a particle size distribution as defined by any other value, range or combination of ranges above. Example 2 of CA 2871398 A1 discloses a particularly preferred manner for the production of a sterile injectable formulation of the present invention, with the proviso that any reference to brexpiprazole dihydrate in CA 2871398 A1 is to be replaced by brexpiprazole dihydrate in the form of crystalline material having a particle size distribution characterized by a d50 of at most 10 µm of the present invention—or by brexpiprazole dihydrate in the form of crystalline material having a particle size distribution as defined by any other value, range or combination of ranges above.

CA 2871398 A1 is hereby incorporated by reference with the proviso that any reference to brexpiprazole dihydrate in CA 2871398 A1 is to be replaced by brexpiprazole dihydrate in the form of crystalline material having a particle size distribution characterized by a d50 of at most 10 µm of the present invention—or by brexpiprazole dihydrate in the form of crystalline material having a particle size distribution as defined by any other value, range or combination of ranges above.

In still a further aspect, the present invention relates to brexpiprazole dihydrate in the form of crystalline material having a particle size distribution characterized by a d50 of at most 10 µm of the present invention—or brexpiprazole dihydrate in the form of crystalline material having a particle size distribution as defined by any other value, range or combination of ranges above—, or to the pharmaceutical composition comprising it for use as a medicament for the treatment of central nervous system disorders, such as for the treatment of schizophrenia.

In still a further aspect, the present invention relates to the use of brexpiprazole dihydrate in the form of crystalline material having a particle size distribution characterized by a d50 of at most 10 µm of the present invention for the preparation of a delayed-release injectable, for example for intramuscular depot formation. Preferably, to the use of brexpiprazole dihydrate in the form of crystalline material having a particle size distribution characterized by a d90 of from 10 µm to 25 µm, such as from 12 µm to 25 µm, or from 15 µm to 22 µm, or alternatively having a particle size distribution characterized by a d50 of from 3 µm to 10 µm, such as from 4 µm to 9 µm, or from 4 µm to 8 µm, or alternatively having a particle size distribution characterized by a d10 of from 400 nm to 3 µm, such as from 600 nm to 2.5 µm, or from 800 nm to 2.0 µm, or alternatively having a particle size distribution characterized by a d90 of from 10 µm to 25 µm, by a d50 of from 3 µm to 10 µm, and by a d10 of from 400 nm to 3 µm, or alternatively having a particle size distribution characterized by a d90 of from 12 µm to 25 µm, a d50 of from 4 µm to 9 µm, and a d10 of from 600 nm to 2.5 µm, or alternatively having a particle size distribution characterized by a d90 of from 15 µm to 22 µm, a d50 of from 4 µm to 8 µm, and a d10 of from 800 nm to 2.0 µm for the preparation of a delayed-release injectable, for example for intramuscular depot formation.

In a further aspect, the present invention relates to a method of evaluating the suitability of a batch of brexpiprazole dihydrate, brexpiprazole dihydrate being in the form of crystalline material having a particle size distribution characterized by a d50 of at most 10 µm, for the preparation of a pharmaceutical delayed-release injectable preparation, comprising the steps of
(1) providing a sample of the batch of brexpiprazole dihydrate;
(2) determining a physicochemical property of the sample, and
(3) determining that the batch is suitable for the preparation of a pharmaceutical delayed-release injectable preparation if the physicochemical property of the sample is consistent with the presence of brexpiprazole dihydrate and the absence of brexpiprazole anhydrate.

Typically the size of the sample is such that the desired physicochemical property can be determined. Preferably more than one sample, for example two or three or more samples of a batch, are tested by determining a physicochemical property.

The physicochemical properties of the sample to be determined in step (2) are properties that are known in the pharmaceutical industry to be capable of characterizing solid forms, such as solid forms of brexpiprazole. Such methods comprise but are not limited to PXRD, FTIR, Raman spectroscopy, DSC, TGA, water content and gravimetric moisture sorption. A preferred method for step (ii) is PXRD.

In step (3) the result from determining the physicochemical property of the sample is analyzed whether it is consistent with the absence of brexpiprazole anhydrate. The presence of brexpiprazole anhydrate can be indicated by the presence of a feature that is indicative of brexpiprazole anhydrate but not of brexpiprazole dihydrate. Such features can be the position and/or form of peaks in FTIR or Raman spectroscopy, which brexpiprazole anhydrate demonstrates, but brexpiprazole dihydrate does not.

Preferably a PXRD of a sample is taken and the diffractogram is evaluated for reflections at 2-theta angles of 6.8°+/−0.2° and 17.4°+/−0.2°. The absence of reflections at 2-Theta angles of 6.8°+/−0.2° and 17.4°+/−0.2° then indicates that the tested batch is suitable. The presence of reflections at 2-Theta angles of 6.8°+/−0.2° and 17.4°+/−0.2° would on the other hand indicate that the batch of brexpiprazole dihydrate is contaminated with brexpiprazole anhydrate and therefore not suitable for the preparation of a pharmaceutical delayed-release injectable preparation.

Alternatively a PXRD of a sample is taken and the diffractogram is evaluated for reflections at 2-theta angles of 10.0°+/−0.2° and 17.4°+/−0.2°. The absence of reflections at 2-Theta angles of 10.0°+/−0.2° and 17.4°+/−0.2° then indicates that the tested batch is suitable. The presence of reflections at 2-Theta angles of 10.0°+/−0.2° and 17.4°+/−0.2° would on the other hand indicate that the batch of brexpiprazole dihydrate is contaminated with brexpiprazole anhydrate and therefore not suitable for the preparation of a pharmaceutical delayed-release injectable preparation.

Alternatively, suitability may be declared if the result from determining the physicochemical property of the sample is consistent with a corresponding reference result obtained from a sample of pure brexpiprazole dihydrate and the absence of any feature which is not consistent with features from pure brexpiprazole dihydrate.

Preferably, also the particle size distribution of the sample is determined and the sample is declared suitable if the crystalline material is confirmed as having a particle size distribution characterized by a d90 of from 10 µm to 25 µm, such as from 12 µm to 25 µm, or from 15 µm to 22 µm, or alternatively a particle size distribution characterized by a d50 of from 3 µm to 10 µm, such as from 4 µm to 9 µm, or from 4 µm to 8 µm, or alternatively a particle size distribution characterized by a d10 of from 400 nm to 3 µm, such as from 600 nm to 2.5 µm, or from 800 nm to 2.0 µm, or a particle size distribution characterized by a d90 of from 12 µm to 25 µm, by a d50 of from 4 µm to 9 µm, and by a d10 of from 600 nm to 2.5 µm, or a particle size distribution characterized by a d90 of from 15 µm to 22 µm, a d50 of from 4 µm to 8 µm, and a d10 of from 800 nm to 2.0 µm.

As disclosed elsewhere herein, the presence of brexpiprazole anhydrate can be indicated by the presence of a feature that is indicative of brexpiprazole anhydrate but not of brexpiprazole dihydrate. An example of such a feature is the position and/or form of peaks in spectroscopy, such as PXRD peaks, which brexpiprazole anhydrate demonstrates, but brexpiprazole dihydrate does not.

As was found in the present invention, when subjecting brexpiprazole dihydrate to a size reduction process, brexpiprazole dihydrate can transform to brexpiprazole anhydrate. Brexpiprazole anhydrate is more soluble than brexpiprazole dihydrate, and also dissolves more quickly upon injection into a mammal. Brexpiprazole anhydrate therefore represents an impurity that in the context of the present invention is desired to be avoided. Thus, in the context of the present invention, it is important to assess whether there is brexpiprazole anhydrate present, e.g. in a batch, and also, in which amount (if it is present).

In order to assess whether e.g. a batch of brexpiprazole dihydrate is suitable for the preparation of a pharmaceutical injectable delayed-release preparation, characteristic PXRD peaks of brexpiprazole anhydrate can be used. If there are PXRD peaks present that are indicative of brexpiprazole anhydrate, then the batch of brexpiprazole dihydrate is declared not suitable for the preparation of said delayed-release preparation.

Thus, in a further aspect, the present invention relates to the use of the PXRD peaks at 2-Theta angles of 10.0°+/−0.2° and 17.4°+/−0.2 of brexpiprazole anhydrate for evaluating the suitability of a batch of brexpiprazole dihydrate, being in the form of crystalline material having a particle size distribution characterized by a d50 of at most 10 µm, for the preparation of a pharmaceutical injectable delayed-release preparation.

The present invention also relates to the use of brexpiprazole dihydrate being in the form of a crystalline, preferably micronized, material having a particle size distribution characterized by a d50 of at most 10 µm in the above method.

Furthermore, the invention also pertains to a process for preparing a batch of brexpiprazole dihydrate comprising less than 5% w/w of brexpiprazole anhydrate in relation to the total amount of brexpiprazole, which batch is suitable for pharmaceutical purposes, preferably for the preparation of a pharmaceutical injectable delayed-release preparation, wherein the process comprises the steps of:
a. providing a batch of brexpiprazole dihydrate in the form of crystalline material having a particle size distribution characterized by a d50 of at most 10 µm, for example by performing the process of preparing brexpiprazole dihydrate as described herein;
b. taking a batch sample and subjecting same to PXRD analysis; and
c. obtaining the batch as a pharmaceutical suitable batch, if reflections at 2-Theta angles of 10.0°+/−0.2° and 17.4°+/−0.2° are absent in the PXRD pattern.

The batch of brexpiprazole dihydrate can, e.g., contain an amount of at least 10 kg.

Finally, the invention refers to a process for preparing a batch of pharmaceutical injectable delayed-release single unit or multiple unit preparations of brexpiprazole dihydrate, the process comprising formulating the batch obtained in the above process into pharmaceutical injectable delayed-release single unit or multiple unit preparations.

Embodiment Section

Aspects, advantageous features and preferred embodiments of the present invention are summarized in the following items:

1. Brexpiprazole dihydrate in the form of crystalline material having a particle size distribution characterized by a d90 of at most 25 μm, the crystalline material comprising less than 5% w/w of brexpiprazole anhydrate in relation to the total amount of brexpiprazole.

2. The brexpiprazole dihydrate of item 1, wherein the crystalline material comprises less than 5% of brexpiprazole anhydrate.

3. The brexpiprazole dihydrate of item 1, wherein the crystalline material comprises no detectable brexpiprazole anhydrate 4. Brexpiprazole dihydrate in the form of crystalline material having a particle size distribution characterized by a d90 of at most 25 μm, in substantially pure form.

5. Brexpiprazole dihydrate in the form of crystalline material having a particle size distribution characterized by a d90 of at most 25 μm, characterized by the absence of an PXRD peak at 10.0°+/−0.2° 2-Theta.

6. Brexpiprazole dihydrate in the form of crystalline material having a particle size distribution characterized by a d90 of at most 25 μm, characterized by the absence of an PXRD peak at at 17.4+/−0.2° 2-Theta.

7. Brexpiprazole dihydrate in the form of crystalline material having a particle size distribution characterized by a d90 of at most 25 μm, characterized by the absence of an PXRD peak at 6.8°+/−0.2° 2-Theta and the absence of an PXRD peak at 17.4°+/−0.2° 2-Theta.

8. Brexpiprazole dihydrate in form of crystalline material having a particle size distribution characterized by a d90 of at most 25 μm, having an PXRD comprising peaks at 2-theta angles of 8.1°, 8.9°, 15.1°, 15.6° and 24.4°, further characterized by the absence of peaks at 2-theta angles of 10.0°+/−0.2° and 17.4°+/−0.2°.

9. Brexpiprazole dihydrate according to any one of items 1 to 8, characterized by a d90 of at most 22 μm.

10. Brexpiprazole dihydrate according to any one of items 1 to 9, characterized by a d90 of from 10 μm to 25 μm 11. Brexpiprazole dihydrate according to any one of items 1 to 10, characterized by a d90 of from 12 μm to 25 μm.

12. Brexpiprazole dihydrate according to any one of items 1 to 11, characterized by a d90 of from 15 μm to 22 μm.

13. Brexpiprazole dihydrate according to any one of items 1 to 12, characterized by a d90 of from 15 μm to 20 μm.

14. A process for the preparation of in the form of crystalline material having a particle size distribution characterized by a d90 of at most 25 μm comprising:
(i) providing brexpiprazole dihydrate in the form of crystalline material having a particle size distribution characterized by a d90 of at least 25 μm;
(ii) adding brexpiprazole dihydrate to an aqueous medium to form a suspension;
(iii) subjecting the aqueous suspension of brexpiprazole dihydrate to a size reduction means to obtain brexpiprazole dihydrate in the form of crystalline material having a particle size distribution characterized by a d90 of at most 25 μm.

15. The process of item 14, wherein pure brexpiprazole dihydrate is used as starting material for step (i).

16. The process according to any one of items 14 to 15, the aqueous medium for forming the suspension in step (ii) is an alcohol/water mixture or water.

17. The process of item 16, wherein the alcohol is a C1 to C4 alcohol.

18. The process according to any one of items 16 to 17, wherein the alcohol is methanol.

19. The process according to any one of items 16 to 18, wherein the alcohol content of the aqueous medium in step (ii) is at most 85% (v/v).

20. The process according to any one of items 16 to 19, wherein the alcohol content of the aqueous medium in step (ii) is at most 80% v/v.

21. The process according to any one of items 16 to 20, wherein the alcohol content of the aqueous medium in step (ii) is at most 70%.

22. The process according to any one of items 14 to 21, wherein the water content of the aqueous medium in step (ii) at least 10% (v/v).

23. The process according to any one of items 14 to 22, wherein the water content of the aqueous medium in step (ii) at least 20% (v/v).

24. The process according to any one of items 14 to 23, wherein the water content of the aqueous medium in step (ii) at least 50% (v/v).

25. The process according to any one of items 14 to 24, wherein the concentration of the brexpiprazole dihydrate applied in (ii) is in the range of from 1% to 60% (w/w).

26. The process according to any one of items 14 to 25, wherein the concentration of the brexpiprazole dihydrate applied in (ii) is in the range of from 2% to 30%.

27. The process according to any one of items 14 to 26, wherein the concentration of the brexpiprazole dihydrate applied in (ii) is about 10%.

28. The process according to any one of items 14 to 27, wherein the means for size reduction in (iii) is wet milling of an aqueous suspension of brexpiprazole dihydrate.

29. The process according to item 28, wherein the milling process of step (iii) is wet ball milling of a suspension of brexpiprazole dihydrate in an aqueous solvent mixture.

30. The process according to any one of items 14 to 29, wherein the temperature for the milling of step (iii) is from −5° C. to 30° C.

31. The process according to any one of items 14 to 30, wherein the temperature for the milling of step (iii) is from −5° C. to 20° C.

32. At least two subsequent batches of brexpiprazole dihydrate according to any one of items 1 to 13 or items 56 to 67.

33. At least three subsequent batches of brexpiprazole dihydrate according to any one of items 1 to 13 or items 56 to 67.

34. The subsequent batches according to any one of items 32 to 33, wherein the brexpiprazole dihydrate is brexpiprazole dihydrate according to any one of items 1 to 13.

35. A pharmaceutical composition comprising brexpiprazole dihydrate according to any one of items 1 to 13 or items 56 to 67.

36. The pharmaceutical composition of item 35 which is an injectable preparation.

37. The pharmaceutical composition according to any one of items 35 to 36, which is a sustained release composition.

38. The pharmaceutical composition according to any one of items 35 to 37, which is a sterile intramuscular injectable.

39. The pharmaceutical composition according to any one of items 35 to 38, further comprising one or more excipient(s) selected from sodium chloride, sodium dihydrogen phosphate, disodium hydrogen phosphate, polyethyleneglycol, polysorbate and polyoxyethylene polypoxypropylene glycol.

40. A sterile injectable pharmaceutical delayed release composition comprising brexpiprazole dihydrate according to any one of items 1 to 13 or items 56 to 67, and two or more excipients selected from sodium chloride, sodium dihydrogen phosphate, disodium hydrogenphosphate, polyethyleneglycol, polysorbate and polyoxyethylene polypoxypropylene glycol.

41. A sterile injectable pharmaceutical delayed release composition comprising brexpiprazole dihydrate according to any one of items 1 to 13 or items 56 to 67, and three or more excipients selected from sodium chloride, sodium dihydrogen phosphate, disodium hydrogenphosphate, polyethyleneglycol, polysorbate and polyoxyethylene polypoxypropylene glycol.

42. A sterile injectable pharmaceutical delayed release composition comprising brexpiprazole dihydrate according to any one of items 1 to 13 or items 56 to 67, and four excipients selected from sodium chloride, sodium dihydrogen phosphate, disodium hydrogenphosphate, polyethyleneglycol, polysorbate and polyoxyethylene polypoxypropylene glycol.

43. A sterile injectable pharmaceutical delayed release composition comprising brexpiprazole dihydrate according to any one of items 1 to 13 or items 56 to 67, and five excipients selected from sodium chloride, sodium dihydrogen phosphate, disodium hydrogenphosphate, polyethyleneglycol, polysorbate and polyoxyethylene polypoxypropylene glycol.

44. A syringe that is filled with an aqueous suspension comprising brexpiprazole dihydrate according to any one of items 1 to 13 or items 56 to 67.

45. A prefilled syringe that is prefilled with an injectable formulation according to any one of items 36 to 43.

46. A method of evaluating the suitability of a batch of brexpiprazole dihydrate, brexpiprazole dihydrate being in the form of crystalline material having a particle size distribution characterized by a d90 of at most 25 µm, for the preparation of a pharmaceutical delayed-release injectable preparation, comprising the steps of
   (i) providing a sample of the batch of brexpiprazole dihydrate;
   (ii) determining a physicochemical property of the sample, and
   (iii) determining that the batch is suitable for the preparation of a pharmaceutical delayed-release injectable preparation if the physicochemical property of the sample is consistent with the presence of brexpiprazole dihydrate and the absence of brexpiprazole anhydrate.

47. The method of item 46, wherein the physicochemical properties of the sample to be determined in step (ii) are selected from PXRD, FTIR, Raman spectroscopy, DSC, TGA, water content and gravimetric moisture sorption.

48. The method according to any one of items 46 to 47, wherein the physicochemical property determined in step (ii) is crystallinity.

49. The method of item 48, wherein crystallinity is determined by PXRD.

50. The method according to any one of items 46 to 49, wherein in step (iii) the result from determining the physicochemical property of the sample is analyzed whether it is consistent with the absence of brexpiprazole anhydrate.

51. The method according to any one of items 46 to 50, wherein in step (iii) the presence of brexpiprazole anhydrate can be indicated by the presence of feature that is indicative of brexpiprazole anhydrate but not of brexpiprazole dihydrate.

52. The method according to any one of items 46 to 51, wherein a PXRD of a sample is taken and the absence of reflections at 2-Theta angles of $6.8°+/-0.2°$ and $17.4°+/-0.2°$ indicates suitability of the tested batch.

53. The method according to any one of items 46 to 51, wherein a PXRD of a sample is taken and the presence of reflections at 2-Theta angles of $10.0°+/-0.2°$ and $17.4°+/-0.2°$ indicates that the tested batch is not suitable for the preparation of a pharmaceutical delayed-release injectable preparation.

54. The method according to any one of items 46 to 53, wherein at least two samples of a batch are tested by determining a physicochemical property.

55. The method according to any one of items 46 to 53, wherein at least three samples of a batch are tested by determining a physicochemical property.

56. Brexpiprazole dihydrate according to any one of items 1 to 8, characterized by a d50 of from 3 µm to 10 µm.

57. Brexpiprazole dihydrate according to any one of items 1 to 8, characterized by a d50 of from 4 µm to 9 µm.

58. Brexpiprazole dihydrate according to any one of items 1 to 8, characterized by a d50 of from 4 µm to 8 µm.

59. Brexpiprazole dihydrate according to any one of items 1 to 8, characterized by a d10 of from 400 nm to 3 µm.

60. Brexpiprazole dihydrate according to any one of items 1 to 8, characterized by a d10 of from 600 nm to 2.5 µm.

61. Brexpiprazole dihydrate according to any one of items 1 to 8, characterized by a d10 of from 800 nm to 2.0 µm.

62. Brexpiprazole dihydrate according to any one of items 1 to 8, characterized by a d90 of from 10 µm to 25 µm, a d50 of from 4 µm to 10 µm, and a d10 of from 400 nm to 3 µm.

63. Brexpiprazole dihydrate according to any one of items 1 to 8, characterized by a d90 of from 10 µm to 25 µm, a d50 of from 4 µm to 10 µm, and a d10 of from 600 nm to 2.0 µm.

64. Brexpiprazole dihydrate according to any one of items 1 to 8, characterized by a d90 of from 10 µm to 25 µm, a d50 of from 4 µm to 10 µm, and a d10 of from 800 nm to 2.0 µm.

65. Brexpiprazole dihydrate according to any one of items 1 to 8, characterized by a d90 of from 12 µm to 25 µm, a d50 of from 4 µm to 9 µm, and a d10 of from 400 nm to 3 µm.

66. Brexpiprazole dihydrate according to any one of items 1 to 8, characterized by a d90 of from 15 µm to 22 µm, a d50 of from 4 µm to 9 µm, and a d10 of from 400 nm to 3 µm.

67. Brexpiprazole dihydrate according to any one of items 1 to 8, characterized by a d90 of from 15 µm to 22 µm, a d50 of from 4 µm to 8 µm, and a d10 of from 800 nm to 2.0 µm.

68. The method of items 46 to 55, wherein also the particle size distribution is determined and wherein the sample is declared suitable if the particle size distribution is confirmed to be a particle size distribution according to any one of items 9 to 13 or 56 to 67.

The invention also refers to the following embodiments, which can be combined with all other embodiments herein:
   a. Brexpiprazole dihydrate in the form of crystalline material having a particle size distribution characterized by a d50 of at most 10 µm, the crystalline material comprising less than 5% w/w of brexpiprazole anhydrate in relation to the total amount of brexpiprazole.

b. The brexpiprazole dihydrate of item a, wherein the crystalline material comprises no detectable brexpiprazole anhydrate.

c. The brexpiprazole dihydrate of item a, characterized by having a PXRD wherein a peak at 10.0°+/−0.2° 2-Theta is absent.

d. The brexpiprazole dihydrate according to any one of items a to c, characterized by having an PXRD comprising peaks at 2-theta angles of 8.1°, 8.9°, 15.1°, 15.6° and 24.4°, and further characterized by the absence of peaks at 2-theta angles of 6.8°+/−0.2° and 17.4°+/−0.2°.

e. The brexpiprazole dihydrate according to any one of items a to d, characterized by a d90 of at most 25 μm.

f. A process for the preparation of brexpiprazole dihydrate in the form of crystalline material having a particle size distribution characterized by a d50 of at most 10 μm comprising:
   (i) providing brexpiprazole dihydrate in the form of crystalline material having a particle size distribution characterized by a d50 of at least 10 μm;
   (ii) adding brexpiprazole dihydrate to an aqueous medium to form a suspension;
   (iii) subjecting the aqueous suspension of brexpiprazole dihydrate to a size reduction means to obtain brexpiprazole dihydrate in the form of crystalline material having a particle size distribution characterized by a d50 of at most 10 μm.

g. The process of item f, wherein the aqueous medium for forming the suspension in step (ii) is an alcohol/water mixture.

h. The process of any one of items f to g, wherein the water content of the aqueous medium in step (ii) at least 10% (v/v).

i. The process according to any one of items f to h, wherein the concentration of the brexpiprazole dihydrate applied in (ii) is in the range of from 5% to 20% (w/w).

j. The process according to any one of items f to i, wherein the means for size reduction in (iii) is wet milling of an aqueous suspension of brexpiprazole dihydrate.

k. At least three subsequent batches of brexpiprazole dihydrate in the form of crystalline material having a particle size distribution characterized by a d50 of at most 10 μm, the crystalline material comprising less than 5% w/w of brexpiprazole anhydrate in relation to the total amount of brexpiprazole.

l. The at least three subsequent batches of brexpiprazole dihydrate in the form of crystalline material having a particle size distribution characterized by a d50 of at most 10 μm of item k, wherein the brexpiprazole dihydrate is brexpiprazole dihydrate according to any one of items a to e.

m. A pharmaceutical sterile injectable sustained release composition comprising brexpiprazole dihydrate according to any one of items a to e.

n. A method of evaluating the suitability of a batch of brexpiprazole dihydrate, brexpiprazole dihydrate being in the form of crystalline material having a particle size distribution characterized by a d50 of at most 10 μm, for the preparation of a pharmaceutical injectable delayed-release preparation, comprising the steps of
   (i) providing a sample of the batch of brexpiprazole dihydrate;
   (ii) determining a physicochemical property of the sample, and
   (iii) determining that the batch is suitable for the preparation of a pharmaceutical delayed-release injectable preparation if the physicochemical property of the sample is consistent with the presence of brexpiprazole dihydrate and the absence of brexpiprazole anhydrate.

o. The method of item n, wherein a PXRD of a sample is taken and the absence of reflections at 2-Theta angles of 10.0°+/−0.2° and 17.4°+/−0.2° indicates suitability of the tested batch.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

The present invention is illustrated in the following examples, which should not be construed as limiting.

EXAMPLES

The powder X-ray diffractogram was obtained with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. The diffractogram was recorded at a tube voltage of 45 kV and a tube current of 40 mA, applying a stepsize of 0.013° 2-Theta with 40 s per step (255 channels) in the angular range of 2° to 40° 2-Theta at ambient conditions. A typical precision of the 2-Theta values is in the range of ±0.2° 2-Theta. Thus, the diffraction peak of form B that appears for example at 14.9° 2-Theta can appear between 14.7 and 15.1° 2-Theta on most X-ray diffractometers under standard conditions.

Raman spectra are recorded with a BRUKER Senterra Raman spectrometer microscope at ambient conditions using a 785 nm laser. A sample is brought to focus with a 20× long working distance objective. Then spectra are collected at 9 to 12 cm$^{-1}$ resolution. A typical precision of the wavenumber values is in the range of from ±1 to ±3 cm$^{-1}$. Thus, a peak at 1591 cm$^{-1}$ for example can appear between 1588 and 1594 cm$^{-1}$ on most Raman spectrometers under standard conditions.

Fourier transform infrared spectrum (FTIR) are recorded (obtained) on an MKII Golden Gate™ Single Reflection Diamond ATR (attenuated total reflection) cell with a Bruker Tensor 27 FTIR spectrometer with 4 cm$^{-1}$ resolution at ambient conditions. To record a spectrum a spatula tip of the sample is applied to the surface of the diamond in powder form. Then the sample is pressed onto the diamond with a sapphire anvil and the spectrum is recorded. A spectrum of the clean diamond is used as background spectrum. A typical precision of the wavenumber values is in the range of about ±2 cm$^{-1}$. Thus, an infrared peak that appears at 1746 cm$^{-1}$ can appear between 1744 and 1748 cm$^{-1}$ on most infrared spectrometers under standard conditions.

DSC is performed on a Mettler Polymer DSC R instrument. An about 3 mg sample is heated in a 40 μL aluminum pan with pierced aluminum lid from 25 to 260° C. at a rate of 10 K/min. Nitrogen (purge rate 50 mL/min) is used as purge gas.

TGA is performed on a Mettler TGA/DSC 1 instrument. The sample is heated in a 100 μL aluminum pan closed with an aluminum lid. The lid is automatically pierced at the beginning of the measurement. The sample is heated from 25 to 240° C. at a rate of 10 K/min. Nitrogen (purge rate 50 mL/min) is used as purge gas.

Moisture sorption/desorption isotherms are recorded with a SPSx-1μ moisture sorption analyzer (Projekt Messtechnik, Ulm). The measurement cycle is started at ambient relative humidity (RH) of 30% and first decreased in one step to 3% RH, then to 0% RH. Subsequently, RH is increased in 10% steps from 0% to 90% RH and further to 95% RH, before decreasing the RH again to 90% RH and further in 10% steps to 0% RH. Finally, the RH is increased to 30% in 10% steps. The time per step is set to a minimum of 2 hours and a maximum of 10 hours. If an equilibrium condition with a constant mass of ±0.01% within 1 hour is reached before the maximum time the sequential humidity step is applied before the maximum time of 10 hours. If no equilibrium is achieved the consecutive humidity step is applied after the maximum time of 10 hours. The temperature is 25.0±0.1° C. The water content of the sample is determined after the moisture sorption/desorption experiment by coulometric Karl-Fischer titration using a Metrohm 831 KF Coulometer.

Particle size distribution was measured with a Malvern Mastersizer 3000 laser diffraction analyzer equipped with a Hydro EV measurement cell. About 50 mg of sample were given into a test tube. The sample was wetted with two drops of Tween 80 and dispersed in about 7 ml of water on a Vortexer. The suspension was treated for 7 minutes in a ultrasonification bath (Elma S50H). The well dispersed suspension was afterwards measured in water at a targeted obscuration range of 10-25 percent while circulating the aqueous suspension and stirring the suspension reservoir at 2000 rpm after a waiting period of three minutes. A fraunhofer optical model was utilized to deconvolute the sample scattering patterns to yield the resultant particle size distributions. Analysis model: General purpose/normal sensitivity. Measuring/background time: about 10 sec Reference Example 1: Preparation of 7-[4-[4-(1-Benzothiophen-4-yl)piperazin-1-yl]butoxy]quinolin-2(1H)-one dihydrate 24 g brexpiprazole anhydrate form I (for example prepared according to the procedure disclosed in comparative example 1 of WO 2013/162046 A1) were charged into a 1 L reactor with jacket, mechanical stirrer, thermometer and condenser. 1000 mL 2-Butanol 90%/10% water (V/V) were added and the suspension was stirred (150 rpm) and heated to a mass temperature of 87.0±0.5° C. A clear solution was obtained. Subsequently the obtained solution was cooled to 60.0° C. in 30 minutes. Brexpiprazole dihydrate seed crystals (for example prepared according to the procedure disclosed in example 1 of WO 2013/162046 A1) were then added under stirring, whereas the mass temperature was kept at 60.0±0.5° C. during the complete addition. Thereafter the suspension was cooled to a mass temperature of 25.0±0.5° C. in 60 min and stirred at the same temperature for 16 hours. Crystallization started after cooling to below 60° C. After crystallization, the suspension was cooled to 0° C. to maximize the yield of Brexpiprazole Dihydrate and further stirred at 150 rpm for 3 hours. The obtained crystalline material was collected by filtration and dried at an air humidity of 43% r.h. over a saturated potassium carbonate solution.

Figure 1:
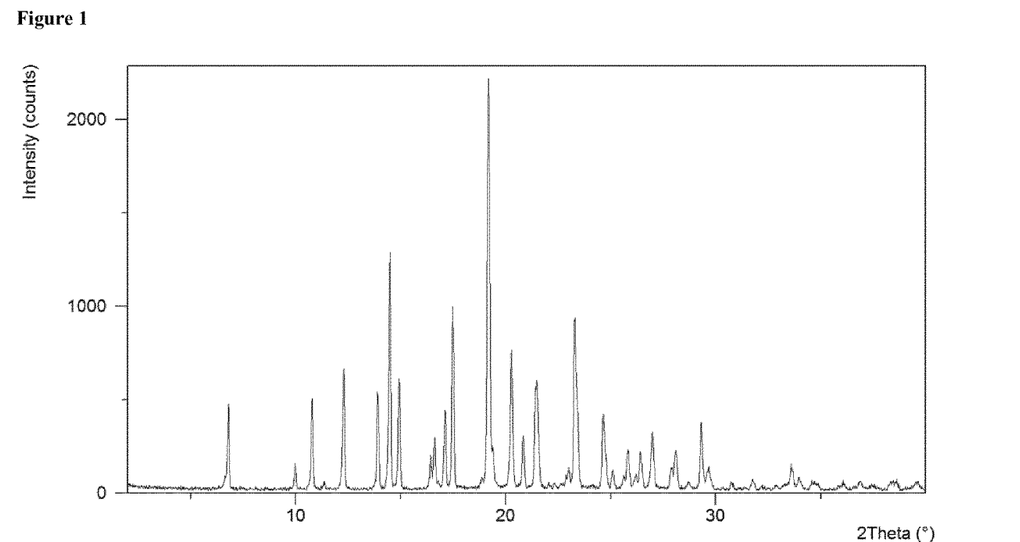
FIG. 1: Representative PXRD of brexpiprazole form I
Figure 2:
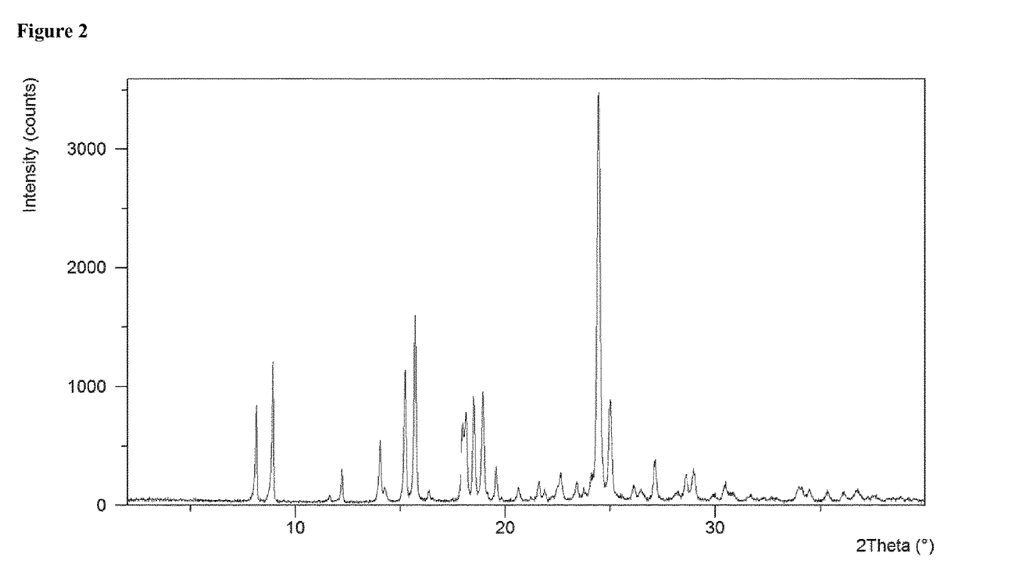
FIG. 2: Representative PXRD of brexpiprazole dihydrate

The obtained crystalline material was analysed by PXRD and PSD. PXRD confirmed that brexpiprazole dihydrate was obtained (FIG. 2). The d90 was above 25 μm as determined by the laser diffraction method in the context of a circulating aqueous suspension as the percent volume at each particle size and measured by a Malvern Mastersizer 3000 laser diffraction analyzer.

Comparative Example 1

900 mg brexpiprazole dihydrate, prepared according to reference example 1, and 100 mg brexpiprazole anhydrate, prepared according to comparative example 1 of WO 2013/162046 A1, were mixed and a PXRD was taken (about 25° C. and 30% relative humidity). FIG. 4 demonstrates that characteristic peaks for both, brexpiprazole anhydrate form I and brexpiprazole dihydrate, were observed. The characteristic PXRD peaks at 10.0° 2-Theta and 17.4 2-Theta were observed in the mixed form I/dihydrate sample only, the characteristic PXRD peak at 6.8° 2-Theta was also observed upon closer inspection.

Example 1

Figure 3A:
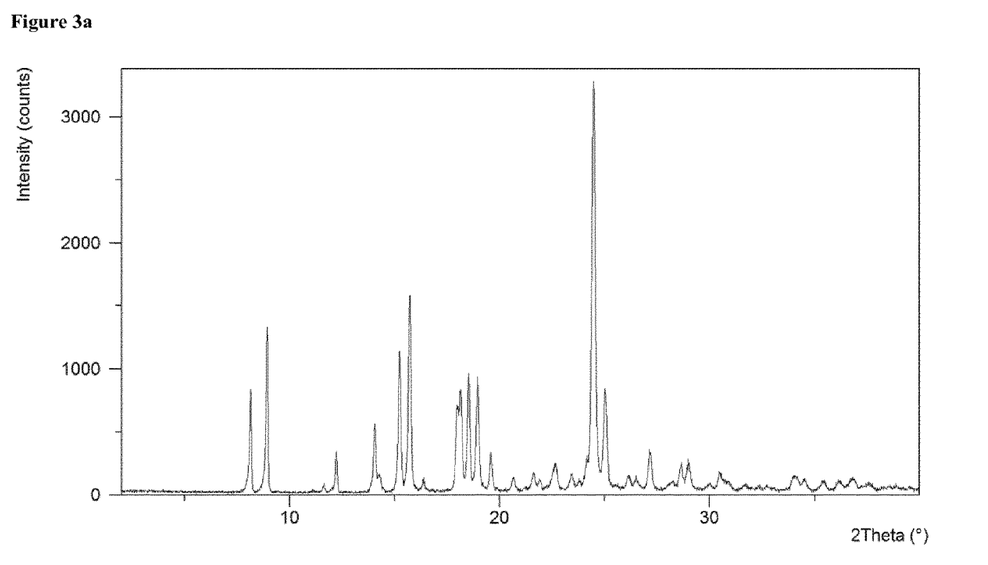
FIG. 3a: Representative PXRD of micronized brexpiprazole dihydrate of the present invention after 5 min micronization

500 mg brexpiprazole dihydrate from comparative example 1 were milled in the presence of 0.2 mL water at 10° C. with a Retsch MM301 ball mill at 25 Hz for 5 min (1.5 ml jacket and 1 steel ball of 5 mm diameter). The obtained micronized crystalline material was analysed by PXRD and PSD. PSD confirmed that micronized brexpiprazole dihydrate was obtained (FIG. 3a). PXRD confirmed that there were no peaks at positions 6.8° and 17.4°, indicating that brexpiprazole dihydrate had not transformed to brexpiprazole anhydrate form I during the micronization process. The obtained micronized brexpiprazole dihydrate had a particle size distribution characterized by a d10 of 1.35 μm, a d50 of 8.24 μm and a d90 of 21 μm. (Determined by the laser diffraction method in the context of a circulating aqueous suspension as the percent volume at each particle size and measured by a Malvern Mastersizer 3000 laser diffraction analyzer.)

Example 2

Figure 3B:
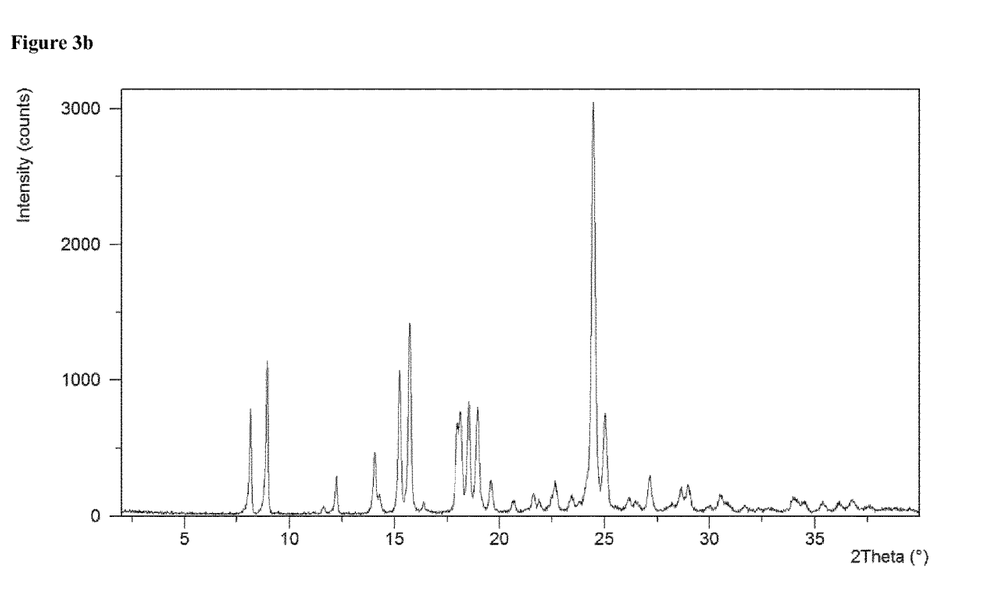
FIG. 3b: Representative PXRD of micronized brexpiprazole dihydrate of the present invention after 15 min micronization

500 mg brexpiprazole dihydrate from comparative example 1 were milled in the presence of 0.2 mL water at 10° C. with a Retsch MM301 ball mill at 25 Hz for 15 min (1.5 ml jacket and 1 steel ball of 5 mm diameter). The obtained micronized crystalline material was analysed by PXRD and PSD. PSD confirmed that micronized brexpiprazole dihydrate was obtained (FIG. 3b). PXRD confirmed that there were no peaks at positions 6.8°, 10.0° and 17.4°, indicating that brexpiprazole dihydrate had not transformed to brexpiprazole anhydrate form I during the micronization process. The obtained micronized brexpiprazole dihydrate had a particle size distribution characterized by a d10 of 1.15 μm, a d50 of 7.04 μm and a d90 of 19 μm. (Determined by the laser diffraction method in the context of a circulating aqueous suspension as the percent volume at each particle size and measured by a Malvern Mastersizer 3000 laser diffraction analyzer.)

Repeated experiments with the above conditions yield micronized brexpiprazole dihydrate in a reproducible manner.

The invention claimed is:
1. A process for preparing a batch of brexpiprazole dihydrate comprising less than 5% w/w of brexpiprazole anhydrate in relation to the total amount of brexpiprazole, which is suitable for pharmaceutical purposes, wherein the process comprises the steps of:

a. providing a batch of brexpiprazole dihydrate by
  (i) providing brexpiprazole dihydrate in the form of crystalline material having a particle size distribution characterized by a d50 of at least 10 μm,
  (ii) adding brexpiprazole dihydrate to an aqueous medium to form a suspension, and
  (iii) subjecting the aqueous suspension of brexpiprazole dihydrate to a size reduction means to obtain brexpiprazole dihydrate in the form of crystalline material having a particle size distribution characterized by a d50 of at most 10 μm;
b. taking a batch sample and subjecting same to PXRD analysis; and
c. obtaining the batch as a pharmaceutical suitable batch, if reflections at 2-Theta angles of $10.0°+/-0.2°$ and $17.4°+/-0.2°$ are absent in the PXRD pattern.

2. The process of claim 1, wherein the batch of brexpiprazole dihydrate contains an amount of at least 10 kg.

3. A process for preparing a batch of pharmaceutical injectable delayed-release single unit or multiple unit preparations of brexpiprazole dihydrate, the process comprising formulating the batch obtained in claim 1 into pharmaceutical injectable delayed-release single unit or multiple unit preparations.

* * * * *